(12) United States Patent
Csincsura et al.

(10) Patent No.: US 7,220,241 B2
(45) Date of Patent: May 22, 2007

(54) COUPLING MECHANISM FOR CONNECTING A CATHETER TO A MEDICAL INFUSION LINE

(75) Inventors: Roland Csincsura, Eisenach (DE); Jörg Heinzerling, Bad Hersfeld (DE)

(73) Assignee: Clinico GmbH, Bad Hersfeld (DE)

( * ) Notice: Subject to any disclaimer, the term of this patent is extended or adjusted under 35 U.S.C. 154(b) by 0 days.

(21) Appl. No.: 11/186,473

(22) Filed: Jul. 21, 2005

(65) Prior Publication Data

US 2006/0030815 A1    Feb. 9, 2006

(30) Foreign Application Priority Data

Jul. 23, 2004   (DE)   ................. 20 2004 011 617 U

(51) Int. Cl.
*A61M 31/00*   (2006.01)
(52) U.S. Cl. .................... 604/93.01; 604/533; 604/180
(58) Field of Classification Search ............ 604/93.01, 604/174, 175, 177, 180, 264, 326, 533–539, 604/502, 506, 164.07; 128/DIG. 6, 26, DIG. 26
See application file for complete search history.

(56) References Cited

U.S. PATENT DOCUMENTS

| 5,522,803 | A |   | 6/1996  | Teissen-Simony |            |
|-----------|---|---|---------|----------------|------------|
| 5,976,115 | A | * | 11/1999 | Parris et al.  | ... 604/533 |
| 6,017,328 | A |   | 1/2000  | Fischell et al.|            |
| 6,123,690 | A |   | 9/2000  | Mejslov et al. |            |
| 6,302,866 | B1| * | 10/2001 | Marggi         | ... 604/174 |
| 6,368,141 | B1|   | 4/2002  | VanAntwerp     |            |
| 6,572,586 | B1| * | 6/2003  | Wojcik         | ... 604/165.01 |
| 2001/0053889 | A1 |  | 12/2001 | Marggi et al. |            |
| 2002/0161332 | A1 | * | 10/2002 | Ramey       | ... 604/164.07 |
| 2003/0216686 | A1 | * | 11/2003 | Lynch et al.| ... 604/93.01 |

FOREIGN PATENT DOCUMENTS

| DE | 198 21 723 | 11/1999 |
| DE | 101 17 285 | 11/2002 |
| DE | 102 55 817 | 6/2004  |
| EP | 0 792 658  | 12/2001 |
| WO | 02/083206  | 10/2002 |

* cited by examiner

*Primary Examiner*—Nicholas Lucchesi
*Assistant Examiner*—Theodore J. Stigell
(74) *Attorney, Agent, or Firm*—Friedrich Kueffner

(57) ABSTRACT

A coupling mechanism for connecting a catheter to a medical infusion line includes a catheter hub arranged on the catheter and a coupling piece arranged at an end of the medical infusion line for connecting with the catheter hub. A pin is axially aligned in the insertion direction of the coupling piece or a sleeve configured for receiving the pin and a locking wedge aligned parallel with the axial extension of the pin or a wedge receptacle for a form-fitting connection of the locking wedge. The wedge receptacle is defined by hinged positive locking elements which are able to move apart from each other. Lever arms are arranged at a distance from each other on the catheter hub or the coupling piece. They interact with the positive locking elements when the coupling mechanism is coupled such that the positive locking elements are spread and the locking wedge is consequently released when the lever arms are actuated.

10 Claims, 2 Drawing Sheets

COUPLING MECHANISM FOR CONNECTING A CATHETER TO A MEDICAL INFUSION LINE

BACKGROUND OF THE INVENTION

1. Field of the Invention

The present invention relates to a coupling mechanism for connecting a catheter to a medical infusion line.

2. Description of the Related Art

In medicine, catheters are used in various fields for administering drugs which have been dissolved or suspended in fluid. Using catheters, medication can be directly administered into the patient's tissue or bloodstream via a puncture site. In order to attach the catheter, it is first necessary to create an entry into the tissue or bloodstream of the patient by means of a puncture. The catheter is then connected to a medical infusion line. In this regard, coupling mechanisms have been designed to permit a fast and secure connection and separation of the catheter and the infusion line.

Such known coupling mechanisms have a catheter hub located on the catheter, on the one hand, and a coupling piece on the infusion line, on the other. For coupling or connecting the line to the catheter, the coupling piece is slid onto the catheter hub, wherein the coupling piece is then appropriately fastened in this position by suitable means, normally by locking. Frequently a coupling cannula in the form of a hollow needle is arranged in the coupling piece. When coupling both the catheter hub and the coupling piece, the cannula serves to pierce the septum located in the catheter hub in order to establish the passage of fluid between the infusion line and the catheter. For this purpose, the coupling cannula is equipped with a sharp (beveled) tip in order to perforate the septum.

It is especially important for self-reliant patients who handle catheters and medical infusion lines on their own such as, for example, insulin patients, to design such coupling mechanisms so that they can be used easily and properly.

This especially requires a secure guidance of the coupling elements (catheter hub and coupling piece) when attaching the coupling mechanism. In this regard, radial forces should particularly be avoided which can lead to, among others, a slipping or detaching of the catheter.

In addition, it is desirable that the patient or other user of the coupling mechanism clearly recognizes the secure locking of the coupling mechanism, for example, by means of an audible sound or tactile sensation.

SUMMARY OF THE INVENTION

Therefore, it is the object of the present invention to provide a coupling mechanism which meets the above described requirements.

To meet this object, a coupling mechanism for connecting a medical infusion line to a catheter is proposed, wherein the catheter is equipped with a catheter hub arranged on the catheter and a coupling piece located at the connection end of the medical infusion line is designed for interacting with the catheter hub, whereby each of the elements (catheter hub or coupling piece, respectively) features one of the following coupling elements, which interact always in pairs.

1. a pin arranged axially in the insertion direction of the coupling piece or a sleeve designed for receiving the pin.

2. a wedge-shaped locking wedge aligned parallel to the axial extension of the pin or a wedge receptacle designed for a form-fitting nesting of the locking wedge, wherein the wedge receptacle is delimited by hinged positive locking elements which can be moved apart from each other for releasing the form-fitting connection between the locking wedge and wedge receptacle, and wherein lever arms are arranged at a distance from each other on that element (connection hub or coupling piece) exhibiting the locking wedge, which interact with the positive locking elements in the coupled state of the coupling mechanism, such that the locking elements are forced apart and the locking wedge is consequently released when the lever arms are actuated.

The coupling mechanism according to the present invention is securely guided by means of the axially aligned pin and sleeve when being joined. The combination of pin and sleeve further provides a firmly fastened positive locking of the coupled coupling mechanism across the axial extension of both of these elements which prevents a detachment of the coupling mechanism in the direction diagonal to this axial direction. A locking of the coupling mechanism in the axial direction is guaranteed by means of the locking wedge and the corresponding wedge receptacle. In addition, since the wedge receptacle is delimited by hinged positive locking elements an audible snapping sound is caused when the wedge is locked into place, so that the user of the coupling mechanism can hear that the coupling mechanism has locked in place properly. Aside from the audible sound the user can also experience a tactile vibration as a result. Furthermore, the lever arms provided, according to the present invention, facilitate an easy release of the connection. By actuating the lever arms the positive locking elements are spread apart and the wedge is released from the wedge receptacle in the process. The coupling mechanism can now be detached by pulling out the coupling piece in the axial direction of the pin/sleeve.

In accordance with a possible solution for the interaction between the lever arms and the positive locking elements, the lever arms are designed as one piece on the element on which they are arranged and are built as two-armed lever arms by means of a film hinge consisting of a narrow material web which is formed between the ends of the lever arms respectively, which connects the lever arm with the remaining element and which divides it into two sections, wherein at least when the coupling mechanism is coupled a first section of the lever arm respectively engages one of the positive locking devices during interaction and a second section of the lever arm serves to actuate the lever arms.

In accordance with a further, more concrete alternative the lever arms each have a guide pin on the first section thereof extending downward in a coupled position (in the direction of the patient's skin surface) which, when the coupling mechanism is coupled, engage the corresponding counterparts in the positive locking elements for spreading the positive locking elements when the second section of the lever arms is actuated. In this embodiment, the guide pins present a simple, yet reliable option for effecting the load transmission from the lever arms to the positive locking elements.

In another embodiment of the coupling mechanism, the lever arms feature grooves on the outer ends of their second sections which when the coupling mechanism is coupled engage the guide webs which are arranged on the element without lever arms and which exhibit a contour such that the grooves are guided on the guide webs when actuating the lever arms, so that aside from the spreading of the positive locking elements a force is exerted in axial direction of the pin/sleeve in a direction of separation on the element on which the lever arms are arranged, which, on the one hand, provides an additional guidance of the coupling piece relative to the catheter hub. On the other, the described contour design of the guide webs already supports or initiates the axial separation when actuating the lever arms. Overall, this leads to a simplified handling of the coupling mechanism including the detaching thereof and reduces the danger of unwanted forces acting on the catheter which could cause pain to the patient or even lead to separation of the catheter and thus the interruption of medication.

In a preferred embodiment of the coupling mechanism, the sleeve and the locking wedge are arranged on the coupling piece and the pin and positive locking elements are arranged on the catheter hub, wherein the axial extension of the pin on the catheter hub extends essentially parallel to the bottom side of the catheter hub to be affixed to the skin surface of the patient. In this embodiment the catheter exhibits an especially flat design, so that it does not unduly stick out beyond from the body surface of the patient and risk getting caught on something.

In another embodiment of the coupling mechanism, the lever arms arranged on the coupling piece stick out to the sides of the coupling piece when in the coupling direction of the elements (catheter hub and coupling piece), while the lever arms embrace the catheter hub in a sickle-shape and rest on the base plate of the catheter when the coupling mechanism is coupled. This embodiment supports, on the one hand, a compact design of the catheter also when hooked up to a medical infusion line. On the other hand, the interaction between the base plate and the lever arms effects an additional guidance of the coupling piece when connecting it with the catheter hub.

Another embodiment of the invention provides that the locking wedge is arranged on the bottom side of the coupling piece facing the patient's skin surface in the coupling direction of the elements and that the positive locking elements are constructed as parts of the base plate which are hinged relative to each other and the base plate by means of material webs or recesses in the base plate. This embodiment additionally entails a compact and small design of the overall coupling mechanism. Due to the fact that the positive locking elements and therefore the wedge receptacle is integrated into the base plate, it is not necessary to provide additional embellishments for forming a wedge receptacle on the catheter hub.

The catheter hub (or the catheter) can be affixed to the skin surface of the patient with an adhesive disk. By means of a notch in the adhesive plate, the adhesive plate can follow the movements of the base plate when the positive locking elements integrated in the base plate are splayed.

Another embodiment includes a pre-perforated septum arranged in the pin/sleeve arranged on the catheter hub which seals off a line element located inside the catheter hub from outside and that a coupling cannula with a rounded penetration tip is arranged in the sleeve/pin arranged on the coupling piece which pierces the septum when the coupling mechanism is coupled. This provides the advantage that no lateral forces act on the coupling mechanism when the coupling cannula pierces the septum contrary to the state of the art when sharp coupling cannulas are employed. The coupling cannula equipped with a rounded penetration tip penetrates the septum axially and straight on without being pressed aside by a beveled section at the sides of the cannula. The septum is pre-perforated so that the rounded coupling cannula can properly pierce the septum.

A cylindrical shape with circular cross-section is preferred as the geometric form for the sleeve and. However, other pin and sleeve geometries with other cross-sections, whether triangular, square or polygon are conceivable and possible.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
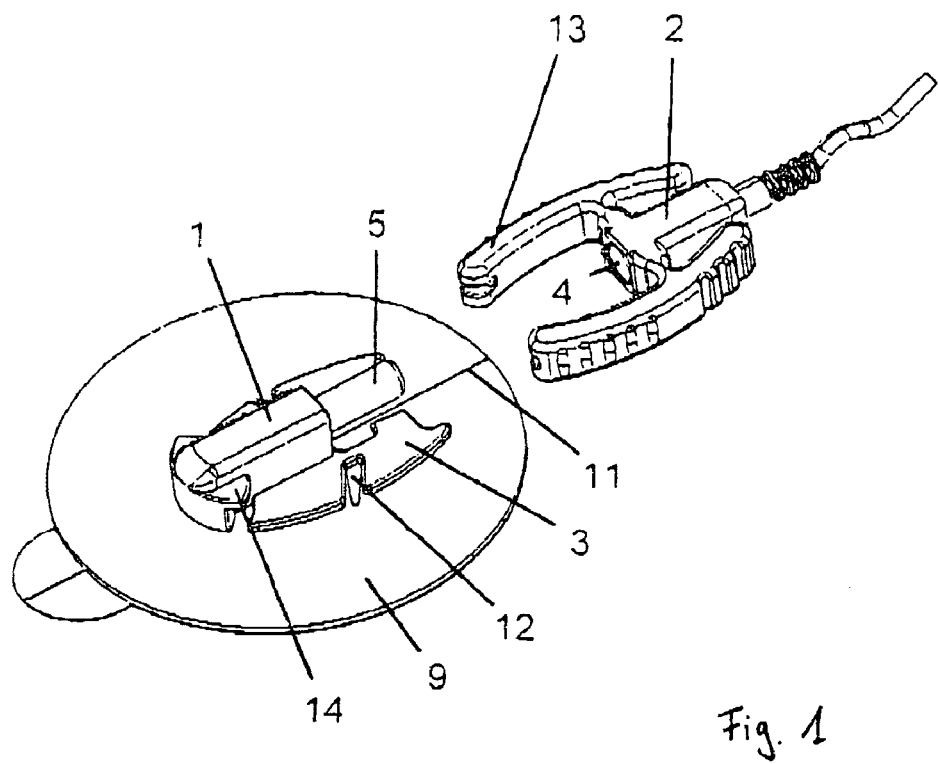
FIG. 1 is a foreshortened view from above of the coupling mechanism with a catheter hub and coupling piece according to the present invention in a separated state.
Figure 2:
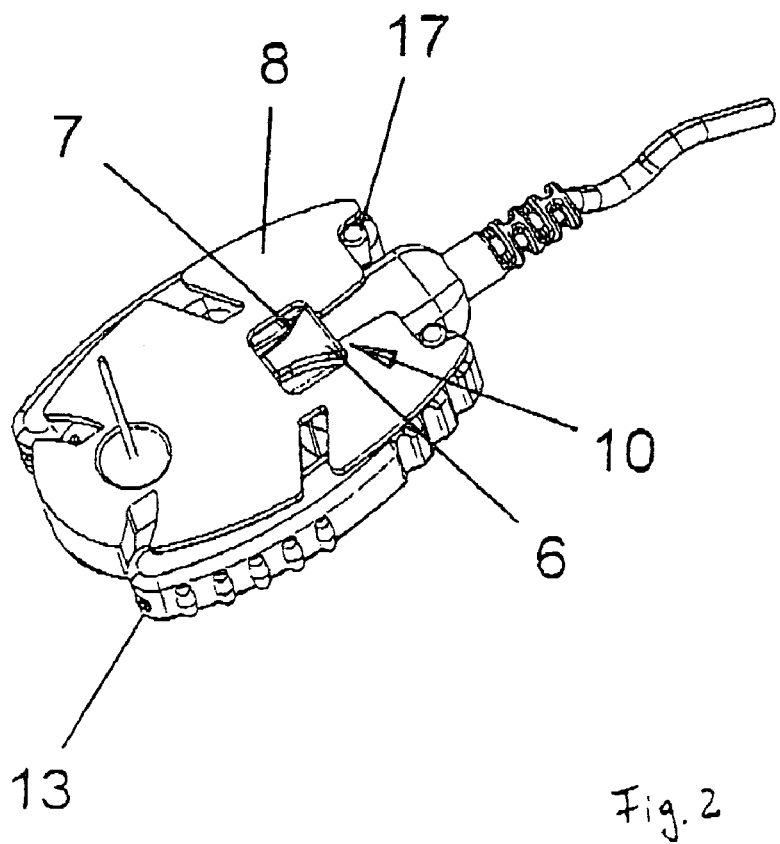
FIG. 2 is a foreshortened, bottom-up view of the coupling mechanism according to the present invention showing the coupling piece coupled with the catheter hub (without the adhesive disk)
Figure 3:
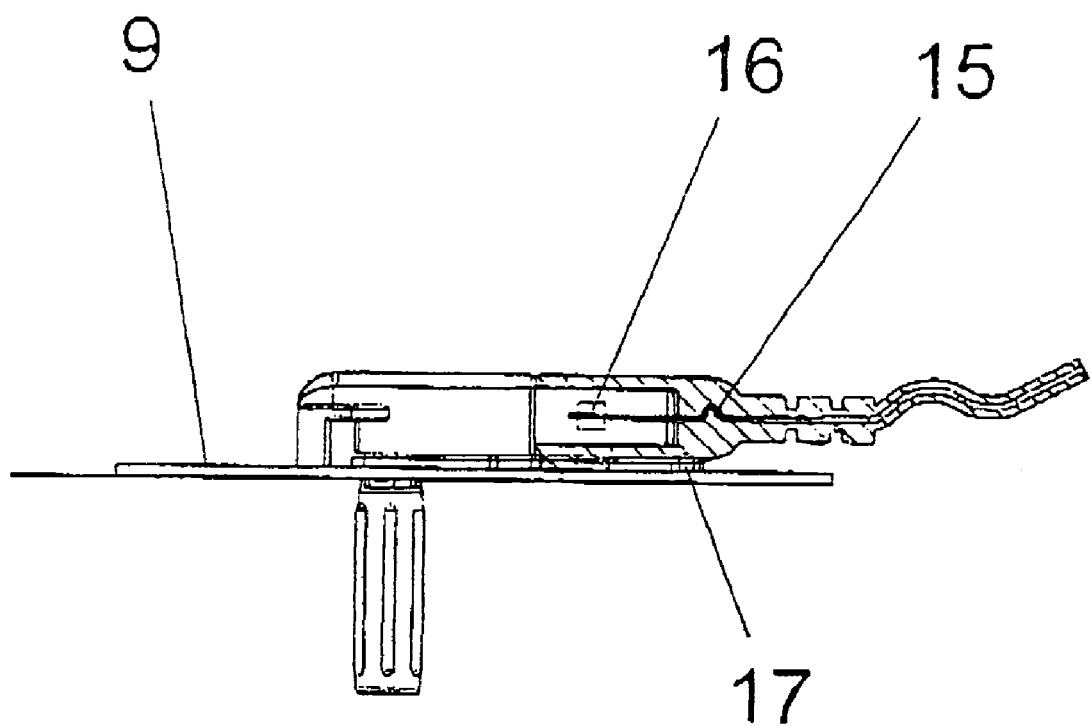
FIG. 3 is a partial cross-sectional side view of the coupling mechanism showing the coupling piece attached to the catheter hub.

FIGS. 1 through 3 show a model of a coupling mechanism according to the present invention from different views. Identical elements are provided with the same reference numbers herein.

The coupling mechanism according to the present invention essentially consists of a catheter hub 1 of a catheter and coupling piece 2 on a medical infusion line.

The catheter hub 1 is attached to the base plate 3 which in turn is affixed to an adhesive disk 9. When applying the catheter, the adhesive disk 9 is affixed to the skin surface of the patient thereby securely fastening the catheter. The catheter hub 1 features a cylindrically-shaped pin 5 with a circular cross-section. The pin 5 extends in an axial direction parallel to the plane of the adhesive disk 9 and consequently parallel to the patient's skin surface when the catheter is affixed to the patient's skin surface in the position of use. A line is led in the interior of the catheter and the catheter hub 1 for inserting the fluid or medication to be administered. In the present example the line is a flexible tube, however, it can also be built, for example, as a rigid steel hollow needle. At one end the line is led into the pin 5 and is there sealed off from its surroundings by means of a septum 16. This septum 16 is pre-perforated for reasons described below. The base plate 3 of the catheter hub 1 features a recess with undercuts in the area below the pin 5 which serves as a wedge receptacle. This wedge receptacle is delimited laterally by the positive locking elements 8 built in the base plate itself. The positive locking elements 8 are connected to the base plate 3 only by means of material webs which at one end are guided from recesses 12 from the outside into the base plate 3. These material webs form hinges around which the positive locking elements 8 are movable in the directions toward or away from each other.

Guide webs 14 with a lenticular shape are located on the end of the catheter hub 1 opposite the pin 5.

The coupling piece 2 exhibits at its center a sleeve 4 with a circular cross-section. This sleeve 4 is designed to mate with the pin 5 of the catheter hub 1 and thus dimensioned accordingly. Outer lever arms 13 are connected in one piece to the coupling piece with thin material webs. These webs are bent convexly and feature slots or grooves at the end opposite the transition of the coupling piece 2 to the medical infusion line. At the other end, i.e., the end facing the medical infusion line, respectively, the lever arms 13 exhibit vertical downward-directed guide pins 17 on the bottom side which faces the patient's skin surface when attaching the coupling piece 2 to the catheter hub 1. On the same bottom side the catheter hub 1 has a locking wedge 6 located centrally under the sleeve which faces with its wedge-shaped, broadened end the end of the coupling piece 2 where the medical infusion line is attached. The lever arms 13 feature a ribbed surface to provide a better hold for handling.

A coupling cannula 15 in the form of a metal hollow needle is connected with the medical infusion line in the interior of the coupling piece 2. This coupling cannula 15 features a rounded puncture tip. The coupling cannula 15 is long enough that it can pierce the septum 16 in the interior of the pin 5 when the pin 5 is completely pressed into the sleeve 4, thereby establishing a connection between the flexible tube in the interior of the catheter and the medical infusion line.

The coupling mechanism according to the present invention works as follows:

For connecting the coupling piece 2 with the catheter hub 1 both elements must first be positioned relative to each other as shown in FIG. 1. The coupling piece 2 with the sleeve 4 is then slid over the pin 5 of the catheter hub 1. The coupling piece 2 is already guided axially in this connection. An additional guidance results from the fact that the lever arms 13 arranged at the side of the coupling piece 2 glide with their bottom side on the base plate 3, which prevents a tilting of the coupling piece. The coupling piece 2 is now slid further forward axially guided on the catheter hub 1 by means of the combination of pin 5 and sleeve 4 until the locking wedge 6 and its lateral radial cams 7 reach the positive locking elements 8 of the base plate 3. With its radial cams 7 the locking wedge 6 splays the positive locking elements 8 which in the process bend apart around the material webs located at the end of the recesses 12. Upon continued pressing of the coupling piece 2 onto the catheter hub 1, the locking wedge 6 completely enters the wedge receptacle delimited by the positive locking elements 8, whereby the positive locking elements 8 snap back into position and lock the locking wedge above the height 10 of the undercuts. The locking wedge 6 is exactly as long as the recess of the wedge receptacle extending from the front end opposite the undercuts to the undercuts. In this position the lever arms 13 with grooves located at their ends have glided over the guide webs 14 and the guide pins 17 engage the formed ridges at the end of the positive locking elements.

When the positive locking elements 8 snap back into position there is a audible snapping sound, so that the user of the coupling mechanism knows that the coupling piece 2 and the catheter hub 1 are properly locked. In addition, the snapping of the positive locking elements 8 can be felt as a tactile sensation, so that the user receives a signal that the connection of the coupling piece 2 and the catheter hub 1 has completed correctly.

When sliding on the coupling piece 2 onto the catheter hub 1 the rounded penetration tip of the coupling cannula 15 pierces the septum 16 which is pre-perforated for this purpose.

In the event that the coupling piece 2 needs to be detached from the catheter hub 1 for example in order to insert and connect a new catheter to a medical infusion line, the lever arms 13 must be pressed together on the ends located at guide webs 14. This causes a splaying of the opposing lever arm ends 13 and the guide pins 17 arranged thereon. The guide pins 17 press apart the positive locking elements 8 in the process, so that the locking wedge 6 is released from the wedge receptacle. At the same time the front ends of the lever arms 13 are slid back in an axial direction (relative to the pin 5 or the sleeve 4) by means of the lenticular shape of the guide webs 14, SO that separation of pin 5 and sleeve 4 is already initiated. The separation process is further assisted by the interaction of the positive locking elements 8 with the radial cams 7 of the locking wedge 6. The positive locking elements 8 snap back toward one another due to resilience of the material webs under load at the end of the recesses 12, as soon as the guide pins 17 are released from the ridges of the positive locking elements 8. In doing so, the locking wedge which in the meantime was withdrawn from the wedge receptacle is moved axially in the separation direction due to the interaction of the positive locking elements 8 and the cams 7. Finally, the user can complete the separation of the coupling. piece 2 and the catheter hub 1 by pulling out the coupling piece 2. The coupling piece 2 can then be used for a renewed connection to the same or another catheter hub 1.

The described coupling mechanism is particularly striking thanks to its simple and safe handling, its audible and tactile locking of the locking wedge 6 in the wedge receptacle, thus providing a distinct signal for the user that the connection was properly established, as well as a secure fitting of the coupling connection both in the axial (relative to the pin 5 and the sleeve 4) and diagonal directions.

We claim:

1. A coupling mechanism for connecting a medical infusion line to a catheter, the mechanism comprising a catheter hub arranged on the catheter and a coupling piece arranged at an end of the medical infusion line for connecting with the catheter hub, wherein one of the catheter hub and the coupling piece has one of a pair of coupling elements which act together in pairs:
   1. a pin axially aligned in an insertion direction of the coupling piece or a sleeve configured for receiving the pin; and
   2. a wedge-shaped locking wedge aligned parallel with an axial extension of the pin or a wedge receptacle for a form-fitting connection of the locking wedge,
   wherein the wedge receptacle is delimited by hinged positive locking elements which are configured to be moved apart from each other for releasing the form-fitting connection between the locking wedge and the wedge receptacle, and wherein lever arms are arranged at a distance from each other on the catheter hub or the coupling piece on which the locking wedge is arranged, which interact with the positive locking elements when the coupling mechanism is coupled such that the positive locking elements are spread and the locking wedge is consequently released when the lever arms are actuated.

2. The coupling mechanism according to claim 1, wherein the lever arms are integrally connected to an element on which they are arranged and are built as two-armed lever arms by means of a film hinge formed between the ends of the lever arms respectively, which connects the lever arm with a remaining element and which divides the lever arm into two sections, wherein at least when the coupling mechanism is coupled, a first section of the lever arm respectively engages one of the positive locking elements during interaction and a second section of the lever arm serves to actuate the lever arms.

3. The coupling mechanism according to claim 2, wherein the lever arms each have a guide pin on the first section thereof extending downward in a coupled position in the direction of the patient's skin surface which, when the coupling mechanism is coupled, engage corresponding counterparts in the positive locking elements for spreading the positive locking elements when the second section of the lever arms is actuated.

4. The coupling mechanism according to claim 1, wherein the lever arms feature grooves on outer ends of their second sections which when the coupling mechanism is coupled engage guide webs arranged on an element without lever arms and which have a contour such that the grooves are guided on the guide webs when actuating the lever arms, so that aside from spreading the positive locking elements a force is exerted in axial direction of the pin/sleeve in a direction of separation on the element on which the lever arms are arranged.

5. The coupling mechanism according to claim 1, wherein the sleeve and the locking wedge are arranged on the coupling piece and the pin and positive locking elements are arranged on the catheter hub, wherein the axial extension of the pin on the catheter hub extends essentially parallel to the bottom side of the catheter hub to be affixed to the skin surface of the patient.

6. The coupling mechanism according to claim 5, wherein the lever arms arranged on the coupling piece stick out to the sides of the coupling piece when in the coupling direction, and wherein the lever arms embrace the catheter hub in a sickle-shape and rest on a base plate of the catheter when the coupling mechanism is coupled.

7. The coupling mechanism according to claim 6, wherein the locking wedge is arranged on a bottom side of the coupling piece facing the patient's skin surface in the coupling direction and wherein the positive locking elements are constructed as parts of the base plate which are hinged relative to each other and the base plate by recesses in the base plate.

8. The coupling mechanism according to claim 7, wherein the catheter hub at the base plate is affixed to an adhesive disk which has a notch in the area of the positive locking elements in order to enable a spreading motion of the positive locking elements.

9. The coupling mechanism according to claim 1, wherein a pre-perforated septum is arranged in the pin or sleeve arranged on the catheter hub which seals off a line element located inside the catheter hub from outside and a coupling cannula with a rounded penetration tip is arranged in the pin or sleeve arranged on the coupling piece which pierces the septum when the coupling mechanism is coupled.

10. A coupling mechanism according to claim 1, wherein the pin is cylindrically shaped and the sleeve is equipped with a correspondingly shaped receiving end opening.

\* \* \* \* \*